(12) United States Patent
Yang et al.

(10) Patent No.: US 10,286,025 B2
(45) Date of Patent: May 14, 2019

(54) **COMPOSITION COMPRISING COMBINED EXTRACTS OF *SCHISANDRA FRUCTUS*, *EUCOMMIAE CORTEX* AND *LYCII FRUCTUS* FOR PREVENTING OR TREATING METABOLIC BONE DISEASES**

(71) Applicant: UNIVERSITY-INDUSTRY COOPERATION GROUP OF KYUNG HEE UNIVERSITY, Yongin-si, Gyeonggi-do (KR)

(72) Inventors: Woong Mo Yang, Seoul (KR); Mi Hye Kim, Gyeonggi-do (KR)

(73) Assignee: University-Industry Cooperation Group of Kyung Hee University, Yongin-Si, Gyeonggi-Do (KR)

( * ) Notice: Subject to any disclaimer, the term of this patent is extended or adjusted under 35 U.S.C. 154(b) by 0 days.

(21) Appl. No.: 15/543,436

(22) PCT Filed: Jan. 15, 2016

(86) PCT No.: PCT/KR2016/000440
§ 371 (c)(1),
(2) Date: Jul. 13, 2017

(87) PCT Pub. No.: WO2016/114621
PCT Pub. Date: Jul. 21, 2016

(65) Prior Publication Data
US 2017/0368127 A1    Dec. 28, 2017

(30) Foreign Application Priority Data

Jan. 15, 2015 (KR) .................. 10-2015-0007395

(51) Int. Cl.
*A61K 36/00* (2006.01)
*A61K 36/79* (2006.01)
*A61K 36/815* (2006.01)
*A61K 36/46* (2006.01)

(52) U.S. Cl.
CPC .............. *A61K 36/79* (2013.01); *A61K 36/46* (2013.01); *A61K 36/815* (2013.01)

(58) Field of Classification Search
CPC ...................................... A61K 36/00
See application file for complete search history.

(56) References Cited

U.S. PATENT DOCUMENTS

2002/0168435 A1 * 11/2002 Kim .................. A61K 36/46
424/769
2007/0264367 A1    11/2007 Kim

FOREIGN PATENT DOCUMENTS

| CN | 103251775 A | * | 8/2013 | |
| JP | 2012077012 A | | 4/2012 | |
| KR | 1020020052034 A | | 7/2002 | |
| KR | 20020086109 A | * | 11/2002 | .............. A61K 36/46 |
| KR | 10-1193540 B1 | | 10/2012 | |
| KR | 10-1194443 B1 | | 10/2012 | |
| KR | 1020130089305 A | | 8/2013 | |
| KR | 10-1305621 B1 | | 9/2013 | |
| KR | 101306408 B1 | | 9/2013 | |

OTHER PUBLICATIONS

Lee, Duck-Joo, Clinical guide for management of osteoporosis, The Korean Journal of Internal Medicine (1999) 57(4):801-4; Partial English translation.
Jerome, Christopher P., "Hormonal therapies and osteoporosis", ILAR J. (2004) 45 (2):170-8.
Belchetz, Paul E., "Hormonal treatment of postmenopausal women", N Engl J Med. (1994) 330 (15): 1062-71.
Lee, Woo Seok, et al., "Prevalence of Osteoporosis in Korean Women", The Journal of Korean Society of Menopause (2003) 9(4):339-46 Abstract.
Neviaser, Andrew S., et al., "Low-Energy Femoral Shaft Fractures Associated with Alendronate Use", Journal of Orthopaedic Trauma (2008) 22(5), 346-350.
Jeong, Bo-seop, et al., Unabridged Dictionary of Native Herbal Medicines, Younglim Publishing Co., pp. 605-606, (1990) Partial English translation.
Yanmei, Li, et al., "The promoting effects of geniposidic acid and aucubin in Eucommia ulmoides Oliver leaves on collagen synthesis", Biological & Pharmaceutical Bulletin (1998) 21(12):1306-1310.
Koo, Yong-Mo, et al., "Effects of Lycii Fructus on the Ovariectomized Osteoporosis of Rats", J. Korean Oriental Med (2008) 29(3):144-154.
International Search Report from PCT/KR2016/000440 dated Jul. 26, 2016.

* cited by examiner

*Primary Examiner* — Qiuwen Mi
(74) *Attorney, Agent, or Firm* — Melissa M. Hayworth; E. Joseph Gess

(57) ABSTRACT

The present invention provides a pharmaceutical composition or a food composition containing combined extracts comprising *Schisandrae fructus*, *Eucommiae cortex* and *Lycii fructus* as active ingredients for preventing or treating metabolic bone diseases. The composition of the present invention does not have side effects as it is a substance derived from natural sources; is effective on osteogenesis in ovariectomized mice; increases the bone content and the bone formation index of serum in real animal model; and reduces the bone resorption index so as to be useful for preventing or treating metabolic bone diseases.

12 Claims, 3 Drawing Sheets

[Fig. 1]
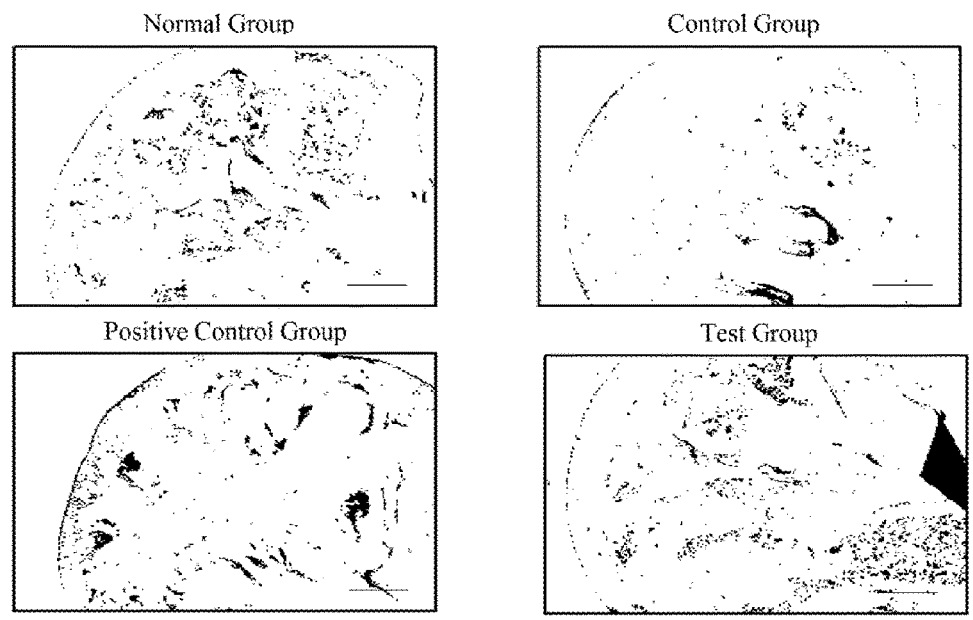

[Fig. 2]
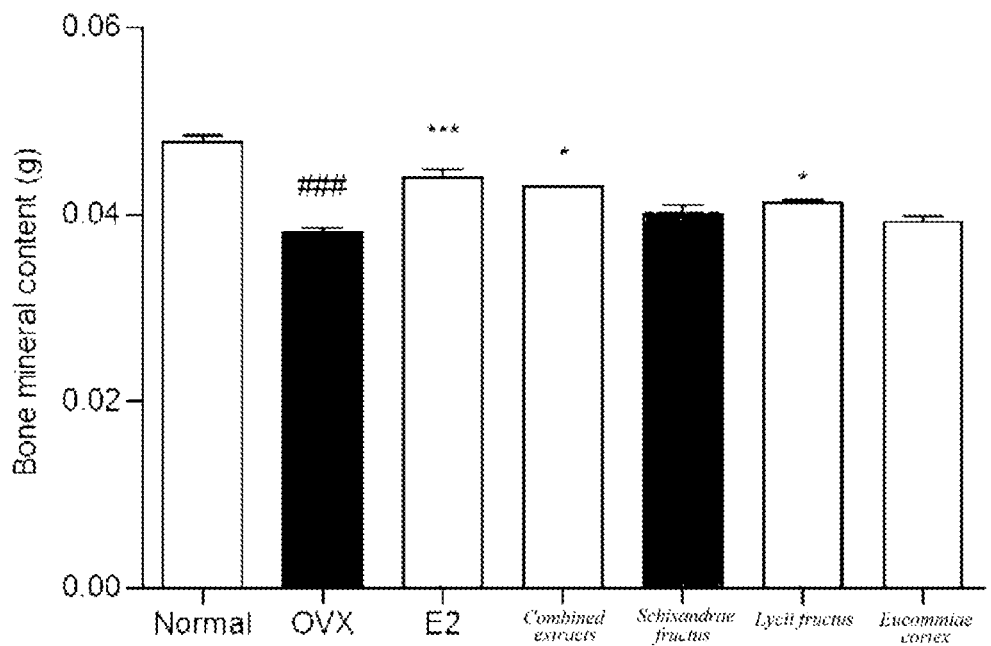
[Fig. 3]
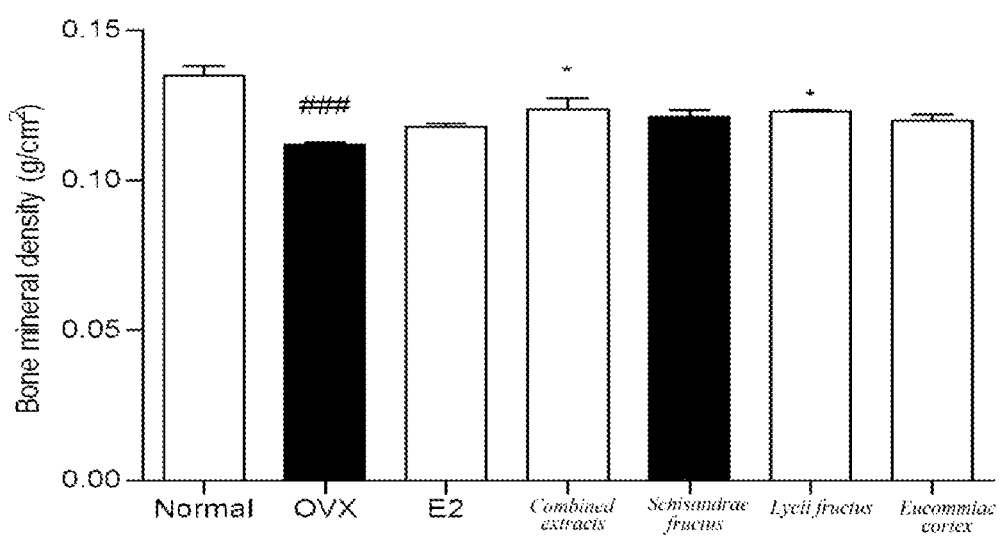

[Fig. 4]
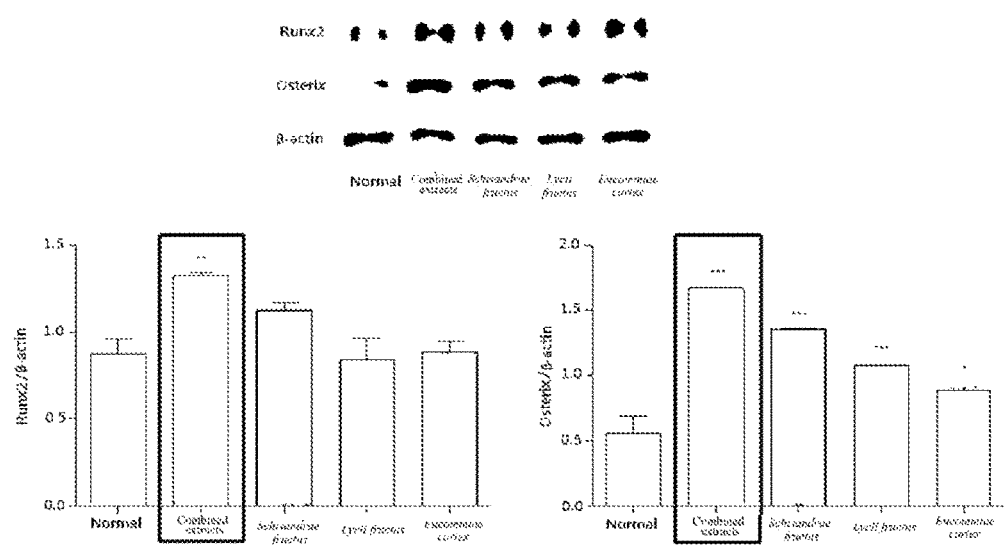

COMPOSITION COMPRISING COMBINED EXTRACTS OF *SCHISANDRA FRUCTUS*, *EUCOMMIAE CORTEX* AND *LYCII FRUCTUS* FOR PREVENTING OR TREATING METABOLIC BONE DISEASES

CROSS-REFERENCE TO RELATED APPLICATIONS

This application is a National Stage Application of PCT/KR2016/000440, filed Jan. 15, 2016, which claims benefit of Korean Patent Application No. 10-2015-0007395, filed Jan. 15, 2015, the contents of all of which are hereby incorporated by reference in their entireties.

TECHNICAL FIELD

The present invention relates to a pharmaceutical composition comprising combined extracts of *Schisandra fructus, Eucommiae cortex* and *Lycii fructus* for preventing or treating metabolic bone diseases.

BACKGROUND ART

Osteoporosis is a disease where bone matrix becomes pathologically lean, and reduces bone mineral density and bone strength, which may consequently increase a risk of broken bones (DJ L. Clinical guide for management of osteoporosis, The Korean Journal of Internal Medicine 1999; 57(4):801-4).

Although bone is made of hard tissues, it is also active and constantly changing throughout our lives. With naked eyes, bone is classified into external cortical bone (compact bone) and internal trabecular bone (cancellous bone), where cortical bone has a physical strength to protect and support the body and trabecular bone is to absorb shocks or maintains calcium changes consistently. Physiologically, bone is also a place where bone remodeling is taking place continuously in order to replace bone matrix to new bone tissues (i.e. bone turnover), which balances it out between bone resorption and bone formation (Jerome C P Hormonal therapies and osteoporosis ILAR J. 2004; 45 (2): . . . 170-8). Thus, the bone mineral density and strength remain steadily in a healthy skeleton because of the bone remodeling that equalizes between bone resorption and bone formation. However, bone remodeling imbalances occur in an osteoporosis-induced bone because of greater bone resorption over bone formation, which leads to decrease in weight and bone mass. Then histologic bone atrophy may occur and skeletal physical strength may also be weakened, which can increase the incidence of fracture (Belchetz P E. Hormonal treatment of postmenopausal women. N Engl J Med. 1994 Apr. 14; 330 (15): 1062-71).

Osteoporosis is a typical metabolic bone disorder, which is caused by the significant quantitative reduction of bone mass, compared to those observed in people of the same age and gender. Riggs and Melton, et al. classified osteoporosis into Type 1 osteoporosis (postmenopausal osteoporosis) or primary osteoporosis, and Type II osteoporosis (senile osteoporosis) or secondary osteoporosis.

Postmenopausal osteoporosis, the Type 1 primary osteoporosis is the most representative metabolic bone disease, and clinically causes more problems such as bone pain, bone fracture and deformity for the elderly (Lee W S PHBD. Prevalence of Osteoporosis in Korean Women. The Journal of Korean Society of Menopause. 2003; 9 (4): 339-46).

Osteoporosis therapeutic agents used these days include bisphosphonate agents (alendronate, etidronate, ibandronate, risedronate, zoledronic, etc.), hormones (raloxifene), vitamin D agents, calcitonin agents, and calcium agents, etc. Recently, parathyroid hormone agents such as Forteo™ are commercially available that are effective on bone formation. However, hormone agents need to be taken throughout the life and there are side effects such as breast cancer, uterine cancer, gallstones and thrombosis when administered a long term. Vitamin D agents are expensive and not reliably effective, and calcitonin agents are expensive and difficult to administer. Although calcium agents have fewer side effects, their functions are limited to preventing rather than treating. Recently commercialized parathyroid hormone agent Forteo™ is effective on bone formation, which compensates shortcomings of existing drugs that only suppress bone resorption. However, Forteo™ needs to be injected every day for a long time and has a side effect of excessive bone formation. It is also too expensive to be widely used.

Thus, the most commonly prescribed osteoporosis medication is from a series of the bisphosphonates. These medications have demonstrated effectiveness in increasing bone mineral density and preventing fracture by intensively suppressing bone resorption. They are also advantageous since they may be administered orally and are cost effective, and thus have been widely used in clinical practices for osteoporosis and other calcium metabolic disorders. However, a bisphosphonate agent has a very complicated intake instruction since it has a low absorption rate and induces esophagitis. Hence it is advised to be taken with plenty of water before breakfast and observe at least 30 minutes of fast, and one shouldn't lie for a certain period of time after the intake. Also, there has been a report the bisphosphonate agent increases the risk of hypocalcaemia.

Recent studies suggest the bisphosphonate agent has clinical problems such as a decreased bone turnover rate resulted from excessive bone resorption inhibition and bone formation inhibition by affecting bone generation rate, gastrointestinal disorder, and jaw bone necrosis. According to a recent research, it may increase the risk of fractures when taken for an extended period of time (Andrew S Neviaser etc., Journal of Orthopaedic Trauma, 2008, 22 (5), 346~350).

Therefore, there has been a need to develop a new substance that has superior efficacy without the above side effects.

*Schisandra fructus* (*Schisandra chinensis*) is characterized as having five distinguishable tastes: sweetness, sourness, bitterness, saltiness, and spiciness, and mainly grows around Mt. Taebaek. *Kadsura* (*Kadsura japonica*) is known to grow in the southern island province, and Black-berry magnolia vine (*Schisandra repanda*) in Jeju Island. *Schisandra chinensis* is known to grow wild in Korea, Japan, Sakhalin Island, and China. *Schisandra fructus* contains ingredients such as schizandrin, gomisin, citral, malic acid, and citric acid that strengthen heart, lower blood pressure and increase the immunity, and it has been used as a cardio-tonic. It is also a known as antitussive and expectorant that effectively relieves coughing and thirst, and enhances the lung function.

Eucommia tree (*Eucommiae cortex* OLIV) is a deciduous tall tree originated from China and belongs to Eucommiaceae. Its dry rhizodermis (根皮) is called *Eucommiae cortex* (杜), and is known to have hypotensive action and diuretic action. Gutta-percha, alkaloid, pectin, jinbang, and resins are known to be included therein (Unabridged Dictionary of Native Herbal Medicines, Bo-seop, Jeong et al., Younglim Publishing Co., p 605-606, 1998), as well as aucubin and geniposide (the promoting effects of geniposidic acid and aucubin in *Eucommiae cortex* Oliver leaves on collagen synthesis./Li Y, Sato T, Metori K, Koike K, Che Q M, Takahashi S/Biological & Pharmaceutical Bulletin [1998, 21 (12): 1306-1310]).

*Lycii fructus* is a fruits from *Lycium chinense* Miller or *Lycium barbarum* Linne, and contains various functional substances such as carotenoids, choline, meliscic acid, zeaxanthin, physalin (dipalmity-zeaxanthin), betaine, β-sitosterol, vitamin B1, rutin and unsaturated fatty acids, etc. Not only that, there are various studies and reports to support that it has anti-oxidant, anti-aging, anti-bacterial and anti-diabetic effects; improves liver function; lowers blood pressure; enhance immune system; lower blood cholesterol; prevent cardiovascular-related disease; and has an anti-cancer effect.

Although there have been disclosures on various extracts comprising the combined extracts comprising *Schisandra fructus*, *Eucommiae cortex* or *Lycii fructus*, there has never been a disclosure relating to combined extracts comprising all of *Schisandra fructus*, *Eucommiae cortex* and *Lycii fructus*. Furthermore, there is no prior art suggesting synergy effect thereof.

DISCLOSURE

Technical Problem

An object of the present invention is to provide a pharmaceutical composition that ensures safety over synthetic chemical substances for preventing or treating metabolic bone diseases.

Technical Solution

The present invention provides a pharmaceutical composition comprising combined extracts of herbal medicine as active ingredients for preventing or treating metabolic bone diseases.

The present invention also provides a food composition comprising combined extracts of herbal medicine as active ingredients for preventing or improving metabolic bone diseases.

Hereinafter, the present invention is explained in detail.
Pharmaceutical Compositions In the present invention, the combined extract of herbal medicine comprises *Schisandra fructus*, *Eucommiae cortex* and *Lycii fructus*.

In the present invention, *Schisandra fructus* may be used from fruits of *Schisandra chinensis*.

In the present invention, *Eucommiae cortex* may be used from dried bark of *Eucommiae cortex* OLIV.

In the present invention, *Lycii fructus* may be used from fruits of *Lycium chinense* or another plant from the same genus.

In the present invention, *Schisandra fructus*, *Eucommiae cortex* and *Lycii fructus* may be mixed in a weight ratio of 1~100:1~100:1~100, and preferably in a ratio of 1~50:1~50:1~50. Also, it is more preferable to mix thereof in a weight ratio of 1~20:1~20:1~20, and most preferable in a weight ratio of 1~10:1~10:1~10. The most superior therapeutic effect is observed in the above ratio.

According to one embodiment of the present invention, the combined extracts of herbal medicines in the present invention may be extracts from the mixture of *Schisandra fructus*, *Eucommiae cortex* and *Lycii fructus*.

According to another embodiment of the present invention, the combined extracts of herbal medicines in the present invention may be the mixture of *Schisandra fructus* extracts, *Eucommiae cortex* extracts, and *Lycii fructus* extracts.

The combined extracts of the present invention may be used after drying the mentioned herbal medicines for 24 to 72 hours, which are washed 1 to 5 times to remove impurities and salt from the surface beforehand. In the present invention, it is preferable to use an extraction solvent selected from a group consisting of water, $C_1$~$C_4$ alcohol, and a mixed solvent thereof. $C_1$~$C_4$ alcohol may be methanol, ethanol, isopropanol, n-propanol, n-butanol, iso-butanol, t-butanol, etc., and methanol or ethanol is most preferred. In case for a solvent mixed with water and $C_1$~$C_4$ alcohol, alcohol contents thereof may be 10% (v/v) to 99% (v/v).

In the present invention, the extract may be concentrated after being extracted with the solvent, and pulverized by lyophilization. Then depending on needs, the solvent extract may be further fractionated with a solvent selected from hexane, methylene chloride, acetone, ethyl acetate, chloroform, and a mixture thereof. At least one type of the above solvents may be used in the fractionation. Shaking extraction, soxhlet extraction or reflux extraction may be used for the extraction method, but not limited thereto. The extract preparing temperature may be 4 □ to 120 □, but not limited thereto. The extraction time is not particularly limited, but may be at least 30 minutes to 7 days, using a conventional hot water extractor, an ultrasonic grinding extractor or a fractionator. The prepared extract may be then filtered under reduced pressure or lyophilized to remove the solvent.

The obtained combined extracts may be stored in a deep freezer before it is ready to use.

Additionally, the combined extracts may completely remove the moisture through the concentrating and lyophilizing process, and may be powdered or dissolved in distilled water or any conventional solvent for its use.

The pharmaceutical composition of the present invention comprising the combined extracts as active ingredients normalized the structure of condyle and reduced an increasing of growth plate thickness in an ovariectomized mice model, compared to thereof found in control group. It also confirmed to increase bone mineral content and bone mineral density, as well as a level of osteocalcin, which is an osteoblasts differentiation factor. Therefore, it was confirmed to be preventive or therapeutic on metabolic bone diseases.

In the present invention, the metabolic bone diseases may be selected from a group consisting of osteoporosis, osteopenia, osteomalacia, osteodystrophy and Paget's disease. Preferably it may be osteoporosis, and more preferably postmenopausal osteoporosis.

The postmenopause osteoporosis is resulted from abnormal hormonal symptoms such as a decrease of estrogen secretion, which strengthens the activity of osteoclast that promotes bone destruction and reduces bone calcification. That is, it is an osteoporosis caused by the weakened activity of osteoblast.

The pharmaceutical composition of the present invention shows an excellent pharmacological activity with no side effects because it contains herbal ingredients, not synthetic chemicals. Therefore, it is safe for a long-term administration.

"Administration" in the present invention refers to introducing the pharmaceutical composition of the present invention to a patient using an appropriate method, and any conventional administration route may be used for the pharmaceutical composition of the present invention as long as it reaches target tissues. The following administration methods are available, but not limited to oral administration, intraperitoneal administration, intravenous administration, intramuscular administration, subcutaneous administration, intradermal administration, intranasal administration, intrapulmonary administration, intrarectal administration, and intrathecal administration. For example, it may be administrated by an oral, rectal or venous, muscular, subcutaneous, intrauterine epidural or cerebral vascular (intracerebroventricular) injection. In addition, the pharmaceutical composition of the present invention may be administered once, or multiple times at regular time intervals.

According to one embodiment of the present invention, the pharmaceutical composition of the present invention may be formulated into a tablet, pill, powder, granule, capsule and etc. for oral administration.

The pharmaceutical composition of the present invention may comprise pharmaceutically acceptable additives such as a diluent, binder, disintegrant, lubricant, pH adjusting agent, antioxidant, and solubilizer within a scope that doesn't damage the effects of the present invention.

As the diluent, sugar, starch, microcrystalline cellulose, lactose (lactose hydrate), glucose, D-mannitol, alginate, alkaline-earth metal salt, clay, polyethylene glycol, anhydrous calcium hydrogen phosphate, or a mixture thereof may be used.

As the binder, starch, microcrystalline cellulose, highly dispersible silica, mannitol, D-mannitol, sucrose, lactose hydrate, polyethylene glycol, polyvinylpyrrolidone (povidone), polyvinyl pyrrolidone copolymers (co-povidone), hypromellose, hydroxypropylcellulose, natural gum, synthetic gum, co-povidone, gelatin, or a mixture thereof may be used.

As the disintegrant, starch or modified starch such as sodium starch glycolate, corn starch, potato starch or pre-gelatinized starch; clay such as bentonite, montmorillonite, or veegum; cellulose such as microcrystalline cellulose, hydroxypropyl cellulose or carboxymethyl cellulose; alginate such as sodium alginate or alginic acid; cross-linked celluloses such as croscarmellose sodium; gums such as guar gum or xanthan gum; crosslinked polymers such as crosslinked polyvinylpyrrolidone (crospovidone); effervescent agents such as sodium bicarbonate or citric acid; or a mixture thereof may be used.

As the lubricants, talc, stearic acid, magnesium stearate, calcium stearate, sodium lauryl sulfate, hydrogenated vegetable oil, sodium benzoate, sodium stearyl fumarate, glyceryl behenate, glyceryl monoolate, glyceryl monostearate, glyceryl palmitostearate stearate, colloidal silicon dioxide, or a mixture thereof may be used.

As the pH adjusting agents, acidifying agents such as acetic acid, adipic acid, ascorbic acid, sodium ascorbate, sodium etherate, malic acid, succinic acid, tartaric acid, fumaric acid citric acid; and alkalizing agents such as precipitated calcium carbonate, aqueous ammonia, meglumine, sodium carbonate, magnesium oxide, magnesium carbonate, sodium citrate and tribasic calcium phosphate may be used.

As the antioxidants, dibutyl hydroxy toluene, butylated hydroxyanisole, tocopheryl acetate, tocopherol, propyl gallate, sodium bisulfite, pyrosulfurous acid sodium may be used.

As the solubilizer, polyoxyethylene sorbitan fatty acid esters such as sodium lauryl sulfate, polysorbate, docusate sodium, and poloxamer, etc. may be used.

Furthermore, according to another embodiment of the present invention, the pharmaceutical composition of the present invention may comprise sterile aqueous solution, non-aqueous solution, suspension, emulsion, lyophilized preparation, and suppository to prepare the formulation for parenteral administration.

Propylene glycol, polyethylene glycol, vegetable oil such as olive oil, and injectable esters such as ethyl oleate may be used as non-aqueous solution or suspension. Witepsol, macrogol, tween 61, cacao oil, laurin oil, glycero-gelatin, etc. may be used as a suppository substrate.

The pharmaceutical composition of the present invention may contain 0.001 to 99.9 wt % of the combined extracts based on the total weight of the composition, preferably contain 0.1 to 99 wt % thereof, and more preferably contain 1 to 50 wt % thereof. However, it may suitably adjust the content of the active ingredients, depending on the method and purpose of its use.

The pharmaceutical composition of the present invention may be administrated orally or parenterally (for example, intravenously, subcutaneously, intraperitoneally, or topically applied), according to the intended method, and dosage thereof may vary depending on the patient's body weight, age, gender, health condition and diet; the time and method of administration; the excretion rate; and the severity of disease. The daily dosage of the combined extracts of the present invention for an adult may be from about 0.001 mg/kg to about 8,000 mg/kg, preferably from about 1 mg/kg to about 4000 mg/kg, more preferably from about 10 mg/kg to about 1000 mg/kg, and most preferably from about 30 mg/kg to about 300 mg/kg.

The pharmaceutical composition of the present invention may comprise at least one or more active ingredient having the same or similar functionality of preventing or treating metabolic bone diseases.

The pharmaceutical composition of the present invention may be used on its own for the prevention or treatment of metabolic bone diseases, or combined with other methods such as a surgical operation, hormonal treatment, drug treatment, and method using a biological response modifier.

In addition, the present invention provides methods for preventing or treating metabolic bone diseases in a mammal including a human by administering the pharmaceutical composition of the present invention.

Food Compositions

The present invention provides a food composition containing combined extracts comprising *Schisandra fructus*, *Lycii fructus* and *Eucommiae cortex* as active ingredients for preventing or improving metabolic bone diseases.

The combined extracts may be prepared in the same way as the pharmaceutical composition of the present invention.

Since the food composition of the present invention has a treatment effect on metabolic bone diseases, it may also be used to prevent or improve the metabolic bone diseases, and the scope of metabolic bone disease is the same as used in the scope of the pharmaceutical composition in the present invention.

The food composition, according to the present invention may be added to the combined extract of the present invention as it is, or further included in conventional additives that may be used in another food compositions, health supplements or drinks.

For example, the food composition of the present invention may comprise sweeteners such as white sugar, crystalline-fructose, glucose, D-sorbitol, mannitol, iso maltooligosaccharides, stevioside, aspartame, acesulfame potassium, and sucralose; acidifiers such as anhydrous citric acid, DL-malic acid, succinic acid and its salt; preservatives such as benzoic acid and derivatives thereof; various nutrients; vitamins; minerals (electrolytes); flavoring agents such as synthetic and natural flavoring agents; coloring agents; enhancers such as cheese, chocolate, etc.; pectic acid and its salts; alginic acid and its salts; organic acid; protective colloidal thickeners; pH adjusting agents; stabilizers; antiseptic; glycerin; alcohol; and carbonated agents used in carbonated drinks. Furthermore, the food composition of the present invention may contain fruit flesh to prepare natural fruit juice and vegetable drinks. The amounts of the additives may be in a range of about 20 parts by weight or less based on 100 parts by weight of the food composition of the present invention.

In case the food composition of the present invention is prepared as drinks, it may further comprise favor or natural carbohydrates. The natural carbohydrates may be monosaccharides such as glucose and fructose; disaccharides such as maltose and sucrose; polysaccharides such as dextrin and cyclodextrin; or sugar alcohols such as xylitol, sorbitol and erythritol. Furthermore, the flavor may include natural flavor such as thaumatin and stevia extract (Rebaudioside A, Glycyrrhizin, etc.); or synthetic flavor such as saccharin, aspartame, etc. When the food composition is prepared in drinks, an amount of about 1 to 20 g (or preferably about 5 to 12 g) of natural carbohydrates is typically contained in every 100 mL of the composition.

The food composition of the present invention may be prepared in a powder, granule, tablet, capsule, or drink form, so it may be administered as food, drink, gum, tea, vitamin complex or health supplements.

Also, the food composition of the present invention may be added to medicine, food and drinks to prevent or improve metabolic bone disorders. For example, the food composition of the present invention may be added to food, drink, gum, tea, vitamin complex, health supplements and the like.

The food composition of the present invention may be added to food or drinks to prevent or improve metabolic bone disorders. The composition of the present invention may be added in an amount of 1 to 5 wt % based on a total weight of the food, and may be added in an amount of 0.02 g to 10 g, and more preferably 0.3 g to 1 g based on every 100 mL of the drink.

Use of the Composition of the Present Invention, and Prevention, Improvement or Treatment of Metabolic Bone Diseases Using Thereof The present invention also provides a use of the combined extract of herbal medicine of the present invention for preparing medicament to prevent or treat metabolic bone diseases, e.g., osteoporosis.

In addition, the present invention provides a method for preventing, improving or treating the metabolic bone diseases by administering the pharmaceutical composition or food composition described above to a subject in need. In the present invention, the subjects include mammals, particularly humans.

The above metabolic bone diseases are the same with the ones described in the disclosure.

Advantageous Effects

No side effects are observed as the combined extracts of the present invention derives from natural sources, and the combined extracts of the present invention reduces an increasing of the growth plate thickness, increases a bone mineral content and bone mineral density, and enhances an expression of osteoblast differentiation factors such as Runx2 and Osterix in an ovariectomized mice model. Therefore, the combined extracts of the present invention may be useful to prevent or treat metabolic bone disorders.

DESCRIPTION OF DRAWINGS

FIG. 1 is a photograph confirming changes in growth plate thickness for femurs in each administration group.

FIG. 2 is a graph comparing changes in a bone mineral content in femurs.

FIG. 3 is a graph comparing changes in a bone mineral density in femurs.

FIG. 4 is a result confirming expressions of Runx2 and Osterix in Saos-2 cells.

BEST MODE

The preferred preparation examples and examples are introduced as follows to help the understanding of the present invention. However, these preparation examples and examples are merely to assist the understanding of the invention, but do not limit the scope of the invention.

Hereinafter, the present invention will be described in further details with reference to examples, but the scope of the present invention is not limited only to the examples. Further, significances amongst control group, comparison group and test group, as per results of the following experiments were compared multiple times using Scheffe method and Bonferroni method after having been verified by ANOVA at a=0.5 level.

Preparation Example 1. Preparation of the Combined Extracts of the Present Invention After having been dried, *Schisandrae fructus*, *Eucommiae cortex*, and *Lycii fructus* purchased from Jeongdosaengyak Co. (Seoul) were measured to what shown in Table 1, and grinded. Then 70% ethanol, which is equivalent of 10 times the weight of the specimen, was added before it was extracted for 24 hours at room temperature. The obtained extract was concentrated under reduced pressure using a rotary vacuum concentrator to obtain concentrates, which would then freeze at −70 □ by a lyophilizer and turn into a powder form. The obtained lyophilized powder is then used as the final extract in the experiments below.

TABLE 1

| | *Schisandrae fructus* | *Eucommiae cortex* | *Lycii fructus* |
|---|---|---|---|
| Preparation Example 1 | 200 g | 100 g | 100 g |

Preparation Examples 2 to 4. Preparing *Schisandra fructus* Extract, *Eucommiae cortex* Extract and *Lycii fructus* Extract Except for extracts that were prepared solely on their own according to the weights indicated in Table 2, single extracts of *Schisandra fructus*, *Eucommiae cortex* and *Lycii fructus* were prepared separately in the same way illustrated in Preparation Example 1.

TABLE 2

|  | Schisandrae fructus | Eucommiae cortex | Lycii fructus |
|---|---|---|---|
| Preparation Example 1 | 400 g | | |
| Preparation Example 2 | | 400 g | |
| Preparation Example 3 | | | 400 g |

MODE FOR INVENTION

Example 1. Confirming Treatment Effects on Metabolic Bone Diseases in Ovariectomized Mice 1-1. Delivering Ovarian Hysterectomy and Medication In order to measure a treatment activity of the combined extracts of Preparation Example 1 on metabolic bone diseases, 28 six-weeks-old white female ICR mice with an average body weight of 30 g (Raon Bio Co., the Republic of Korea) were bred at 22 to 24 □ in temperature and 55 to 60% in relative humidity. The animals were fed with solid feeds (Daehan Biolink Co., the Republic of Korea), and freely accessible to food and water.

Test animals were divided into ① normal group, where suturing operations on stomachs after confirming ovaries by cutting (sham operations) were performed; ② control group (OVX), where ovariosteresis were performed and no drugs were administered; ③ positive control group (E2), where ovariosteresis were performed and estradiol (estradiol; E2), the mammalian estrogen was administered; ④ combined group, where 200 mg/kg of the combined extracts of the present invention (Preparation Example 1) were administered; ⑤ Schisandrae fructus group, where 100 mg/kg of the Schisandrae fructus-only extract of the present invention (Preparation Example 2) was administered; ⑥ Eucommiae cortex group, where 50 mg/kg of the Eucommiae cortex-only extract (Preparation Example 3) was administered; and ⑦ Lycii fructus group, where 50 mg/kg of the Lycii fructus-only extract (Preparation Example 4) was administered.

Ovariosteresis was performed after anesthetizing test animals with a mixture of Zoletil and Rumpun 1:1 (volume ratio). The animals were injected with 0.002 mL of the mixture per 1 g of their body weight. When the animals reached deep anesthesia, ovaries were removed from their incised kidneys that were located at both sides of the spines, and the incision sites were sutured.

The above combined extracts and single extracts were orally administered daily with an experimental specimen where powders shown in Preparation Examples 1 to 4 at a dosage, where powders were dissolved in 200 µl of distilled water, from the sixth week after the ovariosteresis. Normal group and control group were administered with the same amount of distilled water used in the test group. Positive control group was peritoneally administered daily with dosage thereof, along with 10 µg/kg estradiol dissolved in 200 µl distilled water from the sixth week after the ovariosteresis.

1-2. Measuring Thickness of Growth Plate

The collected femoral bone tissues were decalcified in an aqueous formic acid fixed with 10% formalin. An observation area of the bone tissues was dissected by a scalpel, dehydrated in a 70% to 100% of alcohol and acetone, and then washed with xylene before carrying out paraffin-embedding. The paraffin-embedded bone tissues were then sectioned to 5 µm with a microhm and stained with hematoxyline and eosin (H&E), of which result was confirmed with an optical microscope (see FIG. 1).

The thickness of growth plate in the ovariectomized control group (OVX) rapidly surged, compared to the same in normal group, whereas the thickness of femoral growth plate administered with the combined extracts of the present invention was visibly reduced. Therefore, it is proved that the combined extracts of the present invention improves histological symptoms of osteoporosis by suppressing changes in bone tissues.

1-3. Comparing Femoral Bone Mineral Content and Femoral Bone Mineral Density.

The collected femur was used to compare a femoral bone mineral density. The epiphysis of the left femur was dissected, and treated for a dual energy X-ray absorption analysis using a PIXImus device. The femoral bone mineral content (BMC) and the femoral bone mineral density (BMD) obtained from mice in each control group and test group were then compared (see FIG. 2 and FIG. 3).

The bone mineral content and bone mineral density in the ovariectomized control group (OVX) were significantly reduced, compared to normal group thereof. Femoral BMC and BMD were recovered to a comparable level found in positive control group when the combined extracts of the present invention was administered. This confirmed superior efficacy of the combined extracts disclosed in the present invention in comparison with the single extracts of Schisandrae fructus, Eucommiae cortex and Lycii fructus, respectively. Hence, the combined extracts of the present invention may be useful to prevent or treat metabolic bone diseases such as osteoporosis by suppressing BMC and BMD.

Example 2. Confirming Expressions of Runx2 and Osterix in Saos-2 Cells

To confirm expressions of factors associated with osteoblast proliferation, test substances were treated for 24 hours in Saos 2 cells, which are osteoblast-like cell line.

The concentration of the test substance was treated with 100 µg/mL of the combined extract, 50 µg/mL of Schisandrae fructus extract, 25 µg/mL of Lycii fructus extract, and 25 µg/mL of Eucommiae cortex extract. The expression of Osterix and Runx2 (Runt-related transcription factor 2), which is an osteoblast proliferation accelerating factor, was then confirmed by a Western blot assay.

As a result, the combined extracts of the present invention significantly increased the expression of factors associated with osteoblastic proliferation, of which level was remarkably greater than the same in the single administration groups of Schisandrae fructus, Eucommiae cortex and Lycii fructus, respectively.

<Formulation Example> Preparation of the Pharmaceutical Compositions Comprising the Combined Extracts of the Present Invention A. Preparing Powder Formulation
Combined extracts 200 mg
Lactose 100 mg
Talc 10 mg
Mix the above components and fill them in an airtight pack to produce powders.
B. Preparing Tablet Formulation
Combined extracts 200 mg
Corn starch 100 mg
Lactose 100 mg Magnesium stearate 2 mg
Mix the above components and produce tablets by tableting, according to a conventional tablet preparation method.
C. Preparing Capsule Formulation
Combined extracts 200 mg
Crystalline cellulose 3 mg
Lactose 14.8 mg
Magnesium stearate 0.2 mg
Mix the above components and fill them in a gelatin capsule, according to a conventional capsule preparation method.
D. Preparing Injection Formulation
Combined extracts 200 mg
Mannitol 180 mg
Injectable sterile distilled water 2974 mg
$Na_2HPO_4$ $12H_2O$ 26 mg
Prepare each ampule (2 ml) with the above contents, according to a conventional preparation method for injection.
E. Preparing Liquid Formulation
Combined extracts 200 mg
Isomerose 10 g
Mannitol 5 g
Lemon flavouring Appropriate amount
Purified water Appropriate amount
Dissolve the above components in purified water, according to a conventional method for preparing liquid formulation and add an appropriate amount of lemon flavours. Then, blend all and adjust amount thereof with purified water to a total of 100 ml before filling it in a brown bottle and sterilizing thereof.

Simple modifications or changes of the present invention may be easily implemented by a person of ordinary skill in the art, thus such modifications or changes are considered to be included within the scope of the invention.

INDUSTRIAL APPLICABILITY OF THE PRESENT INVENTION

The combined extracts of the present invention may be useful for the prevention or treatment of metabolic bone diseases.

The invention claimed is:

1. A method for preventing or treating metabolic bone diseases comprising administering a pharmaceutical composition consisting of combined extracts coming from a mixture of *Schisandrae fructus, Eucommiae cortex* and *Lycii fructus* as active ingredients to a subject in need.

2. The method according to claim 1 wherein a weight ratio of *Schisandrae fructus, Eucommiae cortex* and *Lycii fructus* is 1~100:1~100:1~100.

3. The method according to claim 1 wherein the extract is extracted with an extraction solvent selected from a group consisting of alcohol, $C_1$~$C_4$ alcohol, and a mixture thereof.

4. The method according to claim 1 wherein the metabolic bone diseases are selected from a group consisting of osteoporosis, osteopenia, osteomalacia, osteodystrophy and Paget's disease.

5. The method according to claim 4 wherein osteoporosis is postmenopausal osteoporosis.

6. The method according to claim 1 wherein the metabolic bone disease is osteoporosis.

7. The method of claim 1, wherein the pharmaceutical composition further contains one or more additives.

8. A method for preventing or improving metabolic bone diseases by administering a food composition consisting of combined extracts coming from a mixture of *Schisandrae fructus, Eucommiae cortex* and *Lycii fructus* as active ingredients to a subject in need thereof.

9. The method according to claim 8 wherein the metabolic bone disease is osteoporosis.

10. The method according to claim 9 wherein osteoporosis is postmenopausal osteoporosis.

11. The method of claim 8, wherein the food composition further contains one or more additives.

12. The method of claim 11, wherein the additive is a sweetener.

* * * * *